United States Patent

Kusaka et al.

Patent Number: 5,283,347
Date of Patent: Feb. 1, 1994

[54] DYE AND ITS SOLUTION

[75] Inventors: Kazuhito Kusaka, Okayama; Sachio Wakayama, Tokyo; Yoshihiro Sekino, Kanagawa; Kazuyoshi Kawazu; Akio Kobayashi, both of Okayama, all of Japan

[73] Assignee: Kabushikikaisha Kibun, Tokyo, Japan

[21] Appl. No.: 754,466

[22] Filed: Sep. 4, 1991

[30] Foreign Application Priority Data

Sep. 4, 1990 [JP] Japan .................................. 2-233879
Aug. 21, 1991 [JP] Japan .................................. 3-209508

[51] Int. Cl.$^5$ ............................................. C07C 50/06
[52] U.S. Cl. ..................................................... 552/304
[58] Field of Search ......................................... 552/304

[56] References Cited

FOREIGN PATENT DOCUMENTS 199766 8/1988 Japan .

OTHER PUBLICATIONS

E. Daimon; Patent Abstracts of Japan; C Field, 12(482):115 C 553 (1988); "Method of Increasing Yield of Red Pigment of Safflower" (Abstract of JP Kokai 63-199766.

N. Ando; Patent Abstracts of Japan; C field, 12(482):4 C 553 (1988); "Carthamin Powder".

T. Enokida; Patent Abstracts of Japan; C field, 13(447):161 C 642 (1989); "Titanium Phthalocyanine Compound, its Production and Electrophotographic Photoreceptor Prepared Therefrom".

*Primary Examiner*—Marianne M. Cintins
*Assistant Examiner*—Kimberly J. Kestler
*Attorney, Agent, or Firm*—Browdy and Neimark

[57] ABSTRACT

Disclosed is a dye having a structural formula (I):

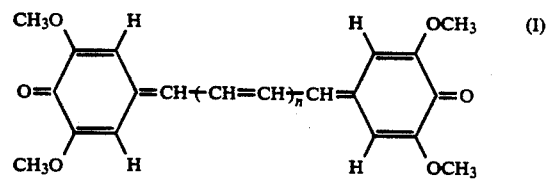

where n is from 1 to 15, and a solution containing the dye. The dye is highly stable and has a characteristic color hue, and it is insoluble in water. The dye is expected to be useful in various fields of coating materials, dyes cosmetics and food additives.

5 Claims, No Drawings

DYE AND ITS SOLUTION

FIELD OF THE INVENTION

The present invention relates to a novel dye and its solution. More precisely, it relates to a novel dye which is highly stable and has a characteristic color hue and which is insoluble in water.

BACKGROUND OF THE INVENTION

A red dye (carthamin) to be extracted from a safflower (*Carthamus tinctorius L.*) is a compound which is useful as a lipstick or rouge or a red-dying substance. However, since extraction of a large amount of carthamin from a safflower is difficult, a method of producing a large amount of carthamin has heretofore been studied earnestly.

Japanese Patent Laid-Open Application Nos. 62-69984, 62-69985 and 63-199766 illustrate methods of producing a mixture containing a red dye by callus-incubation of cells of flower buds of a safflower. The object of the methods is to produce carthamin. As having an Rf value which is extremely near to the Rf value of carthamin, the dye produced by the methods was considered to be carthamin. However, since the dye produced by the methods was not isolated as a pure form, identification as to whether the dye is surely carthamin or not was not made by the prior art.

Under the situation, the present inventors investigated and studied the related arts so as to isolate and identify the dye to be obtained by callus-incubation of cells of flower buds of a safflower. As a result, they have found that the dye formed by such callus-incubation is different from carthamin.

SUMMARY OF THE INVENTION

Surprisingly, the present inventors have found that the dye formed by callus-incubation of cells of flower buds of a safflower is different from carthamin but is a novel compound falling within the scope of the following general formula (I).

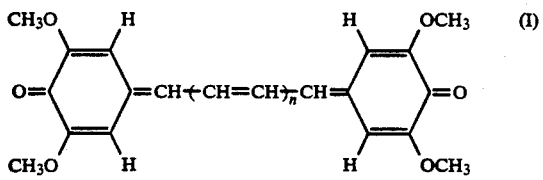

where n is from 1 to 15.

The present invention provides a novel dye compound to be represented by formula (I) and a solution formed by dissolving it in a solvent.

DETAILED DESCRIPTION OF THE INVENTION

Compounds of formula (I0 of the present invention can be obtained, for example, in accordance with the method described in Japanese Patent Laid-Open Application No. 63-199766 where a safflower is cultured by tissue culture, only a component which is soluble in a mixed solvent of acetone/methanol is taken out from the crude product obtained by the culture, and the component is purified by column chromatography. (Examples mentioned below are referred to.) In addition, compounds of formula (I) of the present invention may also be produced by any synthetic methods which are per se well known by those skilled in the art without effecting tissue culture.

The compound of the present invention of formula (I) where n is 1 is a violet pillar-like needle-like crystal, and generally it gives a reddish color when formed into a solution. For instance, a methanol or acetonitrile solution of the compound is red. This is because the compound of formula (I) varies to a limiting structure of the following formula (II) via various structures in its solution.

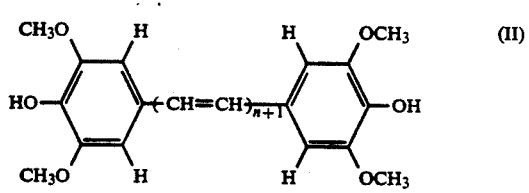

where n is from 1 to 15. (Examples mentioned below are referred to.) Formulae (I) and (II) indicates their limiting structures, and structural conversion between them in a solution is reversible. Therefore, removal of a solvent from the solution of the dye compound again gives a crystal of formula (I). In view of the phenomenon, the compounds of the present invention can be said to have a property suitable for coating and recovery.

The claimed dye solution of the present invention includes all the conditions of crystals of formula (I) as dissolved in a solvent. Accordingly, it is not indispensable that the dye compound exists in the solution in the form having a structure of formula (II) but it may be therein in any other possible form. The both chemical structures of formulae (I) and (II) indicate limiting ones so that the compounds may have various colors in an equilibrated condition between them.

The color of the compounds of the present invention comes to be gradually black from reddish violet via bluish violet with increase of the value of n. Regarding compounds having conjugated double bond(s) in the molecule like compounds of the present invention, it is known that the absorption wavelength is shifted to a long wavelength side almost at certain intervals with prolongation of the conjugated system of the molecule. For instance, for carotinoids such as $\beta$-carotene and linear conjugated alkenes, the maximum absorption wavelength is shifted to a long wavelength side by 20 to 30 nm with increase of one conjugated double bond in the molecule. Accordingly, considering the compounds of the present invention on the basis of the maximum absorption wavelength of them where n is 1 or 2, it is obvious that the compounds where n is at least up to 15 are useful as a dye.

The compounds of the present invention give an extremely noble reddish violet color hue when used for drying silks. It has heretofore been said that such a color hue could hardly be produced by the conventional technical art. Since a color hue varies in accordance with the material to which a dye is applied, a dye solution and a pH value in the dying system, various color hues could be obtained by adequately selecting the conditions.

The compounds of the present invention are well soluble in dimethylsulfoxide, pyridine, methanol, acetonitrile and acetone in this order. They are slightly soluble in acetone but are insoluble in ether, benzene, hexane, carbon tetrachloride and water. Accordingly, the compounds of the present invention are utilized as a water-insoluble hydrophobic dye. The hydrophobicity of the compounds of the present invention increases with increase of the value of n of the molecular formula.

The compounds of the present invention have a characteristic feature that they have a strong binding power to polysaccharides such as cellulose and starch and to proteins. Therefore, the compounds of the present invention are suitable for dying silks and cottons. In addition, since the compounds of the present invention as existing in the solution may well be recovered by adsorbing them to a cellulosic substance, the compounds may be utilized economically. The binding power of the compounds of the present invention to polysaccharides and proteins increases with increase of the value of n of the molecular formula. The compounds of the present invention may further be hydrophobicated, whereby the affinity of the thus hydrophobicated compounds to highly hydrophobic materials may be elevated much.

The compounds of the present invention and solutions of them are excellently stable. For instance, crystals of the compounds do not vary even when stored at room temperature for a long period of time; and a methanol solution of them may also exist stably for a long period of time. The stable property of the compounds of the present invention is contrary to the property of carthamin which rapidly varies to a complex thereof at room temperature and which decomposes in methanol in a short period of time. The excellent stability of the compounds of the present invention could not be anticipated from the fact that they are unstable in a crude product to be obtained by tissue culture of a safflower.

The compounds of the present invention are stable as mentioned above. In order to augment the stability of them, a dye stabilizing agent such as BHT, BHC or an antioxidant may be added to them. If desired, the compounds may be irradiated with UV ray to promote the crosslinking reaction therein so as to further stabilize them. Since UV irradiation often causes variation of the color of the irradiated compounds, it may be effected for the purpose of obtaining dyes having a desired color.

As mentioned above, the compounds of the present invention yield characteristic color hues and have other various characteristics that they have a strong binding power to cellulosic substances and that they are stable and are hardly soluble in water. Because of such characteristic advantages, the compounds of the present invention are expected to effectively and widely useful in various industrial fields of coating materials, dyes, cosmetics and food additives.

Next, the present invention will be explained in more detail by way of the following examples, which, however, are not intended to restrict the scope of the present invention.

EXAMPLE 1

A compound of formula (I) was produced by the process mentioned below.

60 days after sowing of safflower seeds, flower buds of the grown safflower plants swelled slightly. A number of cells were isolated from the flower buds under a sterile condition. A solid medium was separately prepared by adding 9.5 g/liter of agar to Medium (A) mentioned in Table 1 below. The isolated cells of safflower flower buds were dispersed on the solid medium and incubated thereon for 20 days at 25° C. to obtain a large amount of callus.

75 ml of Medium (A) was put in a 300 ml-Erlenmeyer flask and sterilized at 120° C. for 15 minutes. After cooled, 3.5 g of the above-mentioned wet safflower callus was put in the flask and incubated therein at 25° C. for 3 days by rotation culture. Cells as propagated about two times were taken out from the medium by suction filtration, and 3.5 g of them were put on the same medium and were again incubated thereon for further 3 days. The operation was repeated to obtain an active propagated callus.

3.5 g of the thus obtained callus was applied to Medium (B) mentioned in Table 1 below along with an adsorbent (cellulose powder) and incubated at 25° C. for 3 days by rotation culture. After incubation, the callus was separated from the adsorbent (cellulose powder).

TABLE 1

| | Medium (A) (mg/liter) | Medium (B) (mg/liter) |
|---|---|---|
| $KNO_3$ | 1900 | 1900 |
| $NH_4NO_3$ | 1650 | 1650 |
| $KH_2PO_4$ | 170 | 170 |
| $CaCl_2.2H_2O$ | 440 | — |
| $MgSO_4.7H_2O$ | 370 | — |
| $FeSO_4.7H_2O$ | 28 | 28 |
| $Na_2EDTA$ | 37 | 37 |
| $MnSO_4.4H_2O$ | 22 | 22 |
| $ZnSO_4.7H_2O$ | 9 | 9 |
| $H_3PO_3$ | 6 | 6 |
| $CuSO_4.5H_2O$ | 0.025 | 0.025 |
| $NaMoO_2.2H_2O$ | 0.025 | 0.025 |
| KI | 0.83 | 0.83 |
| $CoCl_2.6H_2O$ | 0.025 | 0.025 |
| Myoinositol | 100 | 100 |
| Thiamine.HCl | 10 | 10 |
| Sucrose | 30,000 | 30,000 |
| Naphthaleneacetic Acid | 0.186 | 0.186 |
| Benzyladenine | 0.225 | 0.225 |
| D-phenylalanine | — | 82.5 |

630 g (dry weight) of the colored cellulose powder was stirred in one liter of a mixed solvent of acetone/methanol and filtered. The resulting filtrate was dried up to obtain 520 mg of a solid. 180 mg of the solid was dissolved in methanol and developed through a Sephadex LH20 column (manufactured by Pharmacia) with methanol. The colored fractions were collected and dried to obtain 0.8 mg of a violet pillar-like needle-like crystal.

Melting Point: 228° to 229° C.

IR $(cm^{-1})$ [KBr Method]: 1622, 1605, 1565, 1546, 1308, 1254, 1113

As a result of X-ray diffraction of the crystal obtained, the crystal was identified to be a compound having the structure of formula (I). The crystal did not vary but existed stably, after it was stored at room temperature for at least 150 days.

By dissolution test of the crystal, it was found that the crystal was well soluble in dimethylsulfoxide, pyridine, methanol, acetonitrile and acetone in this order, that it was slightly soluble in ethyl acetate, and that it was insoluble in ether, benzene, hexane, carbon tetrachloride and water. The solution of the crystal was mechanically analyzed to the following results.

$^1H$ NMR [in $(CD_3)_2SO$]: δ3.74 (6H), 3.81 (6H), 6.63 (2H), 7.07 (2H), 7.11 (2H), 7.71 (2H)

UV-VIS [in $CH_3OH$] (nm): 484, 517

MS: M/Z 357 (anion solution mass)

The compound was adsorbed to a cellulose powder and was measured with Color X measuring System Σ80

(manufactured by Nippon Denshoku Co.) to the following results.

L: 70.9 a: 26.5 b: -4.05

EXAMPLE 2

Using the same Medium (A) and Medium (B) as those in Example 1, the same process as in Example 1 was repeated to obtain a cellulose powder having a culture product as adsorbed thereto.

500 g (dry weight) of the cellulose powder was stirred in one liter of a mixed solvent of acetone/methanol (1/1) and filtered. The resulting filtrate was dried up to obtain 260 mg of a solid. The solid was dissolved in methanol and developed through a Sephadex LH20 column (manufactured by Pharmacia) with methanol. The blue dye fraction was further developed on a silica-gel TLC with a mixed solvent developer of benzene/acetone/methanol (7/2/1), whereupon 0.5 mg of a bluish violet crystal was obtained from a fraction having Rf of 0.2.

$^1$H NMR [in acetone D$_6$]: δ3.91 (6H), 3.90 (6H)

UV-VIS [CH$_3$OH] (nm): 565

MS: 385 (cation solution mass; data of reduced form)

While the invention has been described in detail and with reference to specific embodiments thereof, it will be apparent to one skilled in the art that various changes and modifications can be made therein without departing from the spirit and scope thereof.

What is claimed is:

1. A compound having a structural formula (I).

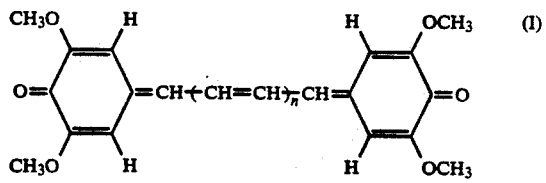

where n is 1 in essentially pure form.

2. A solution comprising a compound as claimed in claim 1 dissolved in a solvent selected from the group consisting of dimethylsulfoxide, pyridine, methanol, acetonitrile and acetone.

3. A solution consisting essentially of the compound of claim 1 as the only dye compound dissolved in a solvent selected from the group consisting of dimethylsulfoxide, pyridine, methanol, acetonitrile and acetone.

4. Violet pillar-like or needle-like crystals of the compound as claimed in claim 1.

5. A composition of matter comprising a compound as claimed in claim 1 free of tissue culture medium.

* * * * *